(12) United States Patent
Smith, Jr. et al.

(10) Patent No.: US 6,995,296 B2
(45) Date of Patent: Feb. 7, 2006

(54) PARAFFIN ALKYLATION

(75) Inventors: Lawrence A. Smith, Jr., Houston, TX (US); Mitchell E. Loescher, Houston, TX (US); John R. Adams, Houston, TX (US); Abraham P. Gelbein, Falls Church, VA (US)

(73) Assignee: Catalytic Distillation Technologies, Pasadena, TX (US)

( * ) Notice: Subject to any disclaimer, the term of this patent is extended or adjusted under 35 U.S.C. 154(b) by 11 days.

(21) Appl. No.: 10/870,104

(22) Filed: Jun. 17, 2004

(65) Prior Publication Data

US 2004/0260136 A1    Dec. 23, 2004

Related U.S. Application Data

(63) Continuation of application No. 10/219,877, filed on Aug. 15, 2002, now Pat. No. 6,858,770.

(60) Provisional application No. 60/313,987, filed on Aug. 21, 2001, provisional application No. 60/323,227, filed on Sep. 19, 2001, provisional application No. 60/334,560, filed on Nov. 30, 2001.

(51) Int. Cl.
*C07C 2/62*    (2006.01)

(52) U.S. Cl. .................. 585/720; 585/723; 585/730
(58) Field of Classification Search ............. 585/332, 585/331, 720, 723, 730
See application file for complete search history.

(56) References Cited

U.S. PATENT DOCUMENTS

| | | | |
|---|---|---|---|
| 2,091,917 A | 8/1937 | Fenske et al. | 196/46 |
| 2,472,578 A | 6/1949 | Ferris et al. | 196/13 |
| 3,155,742 A | 11/1964 | Holzman et al. | 260/683.48 |
| 3,496,996 A | 2/1970 | Osdor | 165/111 |
| 3,725,499 A | 4/1973 | Goldsby | 260/683.62 |
| 3,759,318 A | 9/1973 | Putney et al. | 165/108 |
| 3,839,487 A | 10/1974 | Clonts | 260/633.48 |
| 4,075,258 A | 2/1978 | Caulk et al. | 260/683.53 |
| 4,139,573 A | 2/1979 | Carson | 260/683.49 |
| 4,301,315 A | 11/1981 | Haskell et al. | 585/304 |
| 4,783,567 A | 11/1988 | Kocal | 585/464 |
| 4,891,466 A | 1/1990 | Kocal | 585/464 |
| 5,196,626 A | 3/1993 | Child et al. | 585/720 |
| 5,345,027 A | 9/1994 | Child et al. | 585/720 |
| 5,785,933 A | 7/1998 | Cunningham et al. | 422/224 |
| 6,204,425 B1 | 3/2001 | Hommeltoft | 585/730 |

*Primary Examiner*—Thuan D Dang
(74) *Attorney, Agent, or Firm*—Kenneth H. Johnson (57) ABSTRACT

A process for the alkylation of alkane with olefin or olefin precursor such as an oligomer of tertiary olefin comprising contacting a liquid system comprising acid catalyst, isoparaffin and olefin in concurrent downflow into contact in a reaction zone with a disperser mesh under conditions of temperature and pressure to react said isoparaffin and said olefin to produce an alkylate product is disclosed. Preferably, the liquid system is maintained at about its boiling point in the reaction zone. Unexpectedly, the olefin oligomers have been found to function as olefin precursors and not as olefins in the reaction. Thus, for example, a cold acid alkylation using an oligomer of isobutene (principally dimer and trimer) with isobutane produces isooctane with the isobutane reacting with the constituent isobutene units of the oligomers on a molar basis. The product isooctane is essentially the same as that produced in the conventional cold acid process.

11 Claims, 1 Drawing Sheet

PARAFFIN ALKYLATION

BACKGROUND OF THE INVENTION

This application is a continuation of Ser. No. 10/219,877 filed Aug. 15, 2002 which now U.S. Pat. 6,858,770 claims the benefit of provisional application 60/313,987 filed Aug. 21, 2001, provisional application 60/323,227 filed Sep. 19, 2001 and provisional application 60/334,560 filed Nov. 30, 2001.

FIELD OF THE INVENTION

The present invention relates to the alkylation of paraffinic hydrocarbon feed stocks. The present invention provides both an improvement in the operating conditions and the feed stock for acid paraffin alkylations.

RELATED INFORMATION

The common objective of most alkylation processes is to bring isoalkanes (or aromatics) and light olefins into intimate contact with an acid catalyst to produce an alkylation product. In the petroleum refining industry, acid catalyzed alkylation of aliphatic hydrocarbons with olefinic hydrocarbons is a well known process. Alkylation is the reaction of a paraffin, usually isoparaffins, with an olefin in the presence of a strong acid which produces paraffins, e.g., of higher octane number than the starting materials and which boil in range of gasolines. In petroleum refining the reaction is generally the reaction of a $C_3$ to $C_5$ olefin with isobutane.

In refining alkylations, hydrofluoric or sulfuric acid catalysts are most widely used under low temperature conditions. Low temperature or cold acid processes are favored because side reactions are minimized. In the traditional process the reaction is carried out in a reactor where the hydrocarbon reactants are dispersed into a continuous acid phase.

Although this process has not been environmentally friendly and is hazardous to operate, no other process has been as efficient and it continues to be the major method of alkylation for octane enhancement throughout the world. In view of the fact that the cold acid process will continue to be the process of choice, various proposals have been made to improve and enhance the reaction and, to some extent, moderate the undesirable effects.

U.S. Pat. No. 5,220,095 disclosed the use of particulate polar contact material and fluorinated sulfuric acid for the alkylation. U.S. Pat. Nos. 5,420,093 and 5,444,175 sought to combine the particulate contact material and the catalyst by impregnating a mineral or organic support particulate with sulfuric acid.

Various static systems have been proposed for contacting liquid/liquid reactants, for example, U.S. Pat. Nos. 3,496,996; 3,839,487; 2,091,917; and 2,472,578. However, the most widely used method of mixing catalyst and reactants is the use of various arrangements of blades, paddles, impellers and the like that vigorously agitate and blend the components together, for example, see U.S. Pat. Nos. 3,759,318; 4,075,258; and 5,785,933.

The present application presents a significant advance in the technology relating to alkylation and, in particular, to petroleum refining paraffin alkylation by providing both an effective method for the alkylation, novel olefinic feed and an apparatus for obtaining a high degree of contact between the liquid catalyst and the fluid reactants without mechanical agitation thereby eliminating shaft seals, reducing costs and improving acid product separation.

SUMMARY OF THE INVENTION

There are two aspects to the present invention. The first aspect is a process for the alkylation of paraffin, preferably isoparaffin with olefin or olefin precursor comprising contacting a fluid system comprising acid catalyst, alkane and olefin in concurrent flow, preferably downflow into contact in a reaction zone with internal packing, such as a disperser (as hereinafter described) under conditions of temperature and pressure to react said isoparaffin and said olefin to produce an alkylate product. Preferably, the fluid system comprises a liquid and is maintained at about its boiling point in the reaction zone.

The second aspect of the present invention focuses on the olefin in the alkylation which is characteristic of an olefin precursor. The olefin precursor is an oligomer of one or more tertiary olefins such as the dimer, trimer, etc. of isobutene or a material which corresponds to said oligomer. In a particular embodiment, the present alkylation employs oligomers of tertiary olefins as the olefin component of the alkylation with isoalkanes.

It has been surprisingly discovered that olefin reactants that correspond to oligomers of olefins (for example, the longer chain oligomers of olefins made by polymerizing shorter chain olefins) when reacted in an acid alkylation with an isoalkane react on a molar basis with the constituent olefins of the oligomer, rather through the oligomers, per se, to produce alkylate product of the constituent olefin(s) and the isoalkane and not the alkylate of the oligomer per se as expected. The reaction may be carried out in an apparatus comprising a vertical reactor containing a disperser or other suitable packing in the reaction zone which may comprise the entire column or a portion thereof.

DETAILED DESCRIPTION OF THE INVENTION

Figure 1:
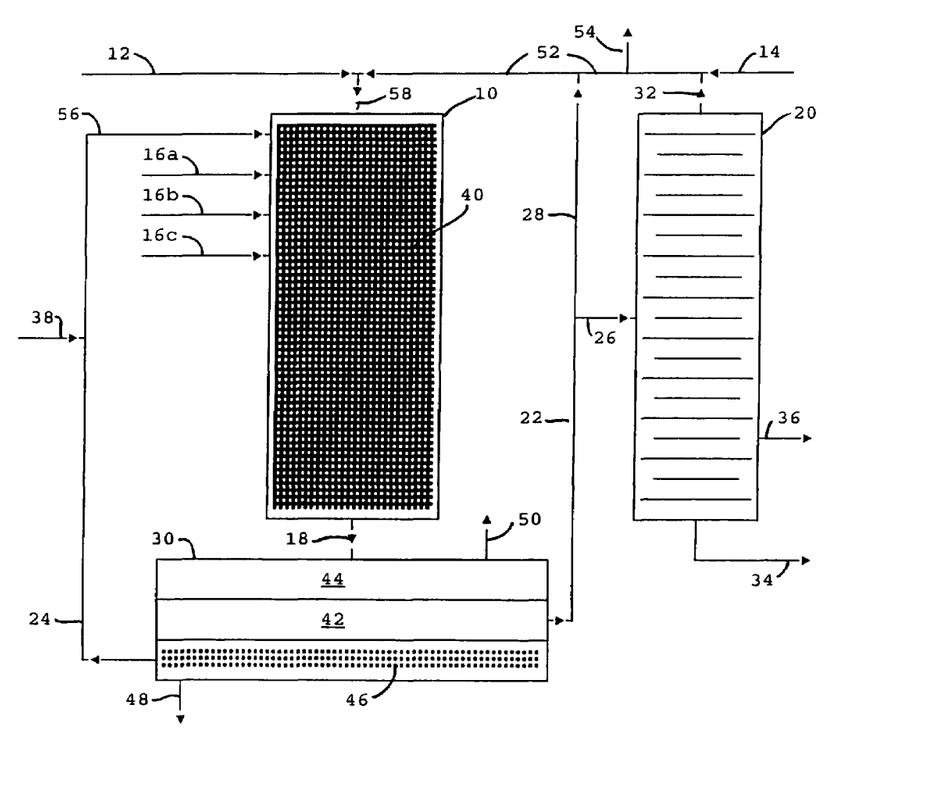
The FIGURE is a schematic representation of the first aspect of the present apparatus in which the present alkylation process may be carried out.

The reaction of oligomer of tertiary olefins with isoalkanes is on a molar basis with the constituent tertiary olefins of the oligomer rather than the oligomers. The alkylate product corresponds to the reaction of the tertiary olefin and isoalkanes.

For the purpose of illustration and not a limitation of the process, it is believed that instead of the expected reaction between the oligomer and the isoalkane, the oligomer is cracked into its olefin components which react with the isoalkane on a molar basis:

1) diisobutene+2 isobutane→2 isooctane (2,2,4-trimethyl pentane)
2) triisobutene+3 isobutane→3 isooctane (2,2,4-trimethyl pentane)

The conventional view had been that the product of 1) would be a $C_{12}$ alkane and the product of 2) would be a $C_{16}$ alkane whereas the product of reactions 1) and 2) is the same and is indistinguishable from a conventional cold acid alkylation product of the reaction:

3) 2 butene-2+2 isobutane→2 isooctane
4) 3 butene-2+3 isobutane→3 isooctane

The great advantage of the present invention is that although acid alkylations are extremely exothermic and require substantial refrigeration to maintain the reaction temperature in optimum range to prevent side reactions, the present reaction of the oligomers with the isoalkane to produce the alkylate in the same yields required less refrigeration making the process less expensive for the same yield of useful product.

One particular method of producing oligomer is that carried out in a catalytic distillation, for example, units formerly used to produce MTBE can readily be converted to producing oligomer merely by changing the feed to the reactor since the same catalyst serves both reactions.

Preferably, the oligomer comprises $C_8$ to $C_{16}$ olefins corresponding to oligomer prepared from $C_3$ to $C_5$ olefin. In a preferred embodiment the oligomer has 6 to 16 carbon atoms and corresponds to oligomers which are prepared from $C_4$ to $C_5$ olefins.

The widest use of the paraffin alkylation is for the preparation of a $C_8$ gasoline component. The feed to this process is usually normal butene and tertiary butane contained in a "cold acid" reaction usually with sulfuric acid or HF. The normal butene (butene-2, for example) is a component of light naphtha along with normal butane, isobutane and tertiary butene. The separation of the normal butene from the isobutene can be effected by fractionation with difficulty because of their close boiling point. A preferred way to separate these olefin isomers or those of the $C_5$ analogs is to react the more reactive tertiary olefin to form a heavier product which is easily separated from the normal olefins by fractionation.

Heretofore, the tertiary olefin was reacted with a lower alcohol, such as methanol or ethanol, to form ethers, such as methyl tertiary butyl ether (MTBE), ethyl tertiary butyl ether (ETBE), tertiary amyl methyl ether (TAME) which have been used as gasoline octane improvers but are being phased out because of health concerns.

The oligomerization of the tertiary olefin is also a preferred reaction when carried out on a naphtha stream with the separation of normal olefin being easily achieved by fractionation from the heavier (higher boiling) oligomers (mainly dimer and trimer). The oligomers may be used as gasoline components but there are limits to the amount of olefin material desirable or allowed in gasoline and it is frequently necessary to hydrogenate the oligomers for use in gasoline. The most desirable component for gasoline blending is $C_8$, e.g., isoctane (2,2,4 trimethyl pentane).

The oligomer may be cracked back to the original tertiary olefins and used in cold acid reaction. However, the present invention has found that it is not necessary to crack the oligomer which may constitute the olefin feed to cold acid reaction with the alkane or may be co-fed with mono olefins. As noted above the result is the same product as the mono olefin alone with the additional benefit of a less exothermic overall reaction requiring less refrigeration and, hence, a lower energy cost for the alkylation.

The oligomerization process produces a heat of reaction that does not require the magnitude of heat removal as in the cold acid process. In fact, when the oligomerization is carried out in a catalytic distillation type reaction, the heat of reaction is removed as boilup, which in this type of reaction is the lower boiling mono olefins and alkanes which are being separated from the oligomer. Thus, even though there is heat produced in the oligomerization it is of no cost to the production of the gasoline since it is used in the fractionation, and the operating cost of the alkylation unit is reduced by the use of oligomer to replace some or all of the conventional short chain olefin.

In a preferred embodiment of the present alkylation process, a light naphtha stream comprising normal and tertiary olefins is contacted with an acid resin catalyst under oligomerization conditions to preferentially react a portion of the tertiary olefins with themselves to form oligomers, and feeding said oligomers to an alkylation zone with an isoalkane in the presence of an acid alkylation catalyst to produce an alkylation product comprising the alkylate of said tertiary olefin and said isoalkane.

The oligomerization may be carried out in a partial liquid phase in the presence of an acid cation resin catalyst either in straight pass type reaction or in a catalytic distillation reaction where there is both a vapor and liquid phase and a concurrent reaction/fractionation. Preferably, the feed is a $C_4$–$C_5$, $C_4$ or $C_5$ light naphtha cut. The tertiary olefins may include isobutene, and isoamylenes and are more reactive than the normal olefin isomers and are preferentially oligomerized. The primary oligomer products are dimers and trimers. The isoalkanes preferably comprise isobutane, isopentane or mixtures thereof.

When a straight pass reactor is used, such as that disclosed in U.S. Pat. Nos. 4,313,016; 4,540,839; 5,003,124; and 6,335,473, the entire effluent comprising the oligomer, normal olefins and isoalkanes may be fed to an acid alkylation reaction. The normal alkanes are inert under the conditions of the present alkylation. Under alkylation conditions the isoalkane reacts with the normal olefin to form alkylate product and with the individual constituent olefins of the oligomers to form the alkylate product. The implication of the result of the present process is that the oligomers are dissociated or in some manner make their constituent olefins available for reaction with isoalkanes. Thus, the reaction will produce:

1) isobutene oligomer+isobutane→isooctane;
2) isobutene oligomer+isopentane→branched $C_9$ alkanes;
3) isoamylene oligomer+isobutane→branched $C_9$ alkanes;
4) isoamylene oligomer+isopentane→branched $C_{10}$ alkanes;

whereas it would have been expected that reaction 1) would produce at least or mostly $C_{12}$ alkanes, reaction 2) would produce at least or mostly $C_{13}$ alkanes, reaction 3) would produce at least or mostly $C_{14}$ alkanes, and reaction 4) would produce at least or mostly $C_{15}$ alkanes.

When a catalytic distillation reaction such as that disclosed in U.S. Pat. Nos. 4,242,530 or 4,375,576 is employed for the oligomerization, the oligomer is separated from the lower boiling normal olefins and alkanes in the reaction product by concurrent fractionation. The streams, normal olefins and alkanes (overheads) and oligomers (bottoms), may be united or individually fed to the alkylation or may be used individually with at least the oligomer being fed to the alkylation.

The present invention offers an improved contacting apparatus and process for producing and separating an alkylate product using sulfuric acid as catalyst. This same or similar device may also be used with other acids or acid mixtures.

The present process preferably employs a downflow reactor packed with contacting internals or packing material (which may be inert or catalytic) through which passes a concurrent multi phase mixture of sulfuric acid, hydrocarbon solvent and reactants at the boiling point of the system. The system comprises a hydrocarbon phase and an acid/hydrocarbon emulsion phase. A significant amount of sulfuric acid is held up on the packing. Reaction is believed to take place between the descending hydrocarbon phase and the sulfuric acid dispersed on the packing. Olefin continuously dissolves into the acid phase and alkylate product is continuously extracted into the hydrocarbon phase. Adjusting the pressure and hydrocarbon composition controls the boiling point temperature. The reactor is preferentially operated vapor continuous but may also be operated liquid continuous. The pressure is preferentially higher at the top of the reactor than at the bottom.

Adjusting the flow rates and the degree of vaporization controls the pressure drop across the reactor. Multiple injection of olefin is preferred. The type of packing also influences the pressure drop due to the acid phase hold-up. The product mixture before fractionation is the preferred circulating solvent. The acid emulsion separates rapidly from the hydrocarbon liquid and is normally recycled with only a few minutes residence time in the bottom phase separator. Because the products are in essence rapidly extracted from the acid phase (emulsion), the reaction and/or emulsion promoters used in conventional sulfuric acid alkylation processes may be added without the usual concern for breaking the emulsion. The process may be described as hydrocarbon continuous as opposed to acid continuous.

Preferably, the disperser comprises a conventional liquid-liquid coalescer of a type which is operative for coalescing vaporized liquids. These are commonly known as "mist eliminators" or "demisters", however, in the present invention the element functions to disperse the fluid materials in the reactor for better contact. A suitable disperser comprises a mesh such as a co-knit wire and fiberglass mesh. For example, it has been found that a 90 needle tubular co-knit mesh of wire and multi-filament fiberglass such as manufactured by Amistco Separation Products, Inc. of Alvin, Texas, can be effectively utilized, however, it will be understood that various other materials such as co-knit wire and multi filament teflon (Dupont™), steel wool, polypropylene, PVDF, polyester or various other co-knit materials can also be effectively utilized in the apparatus. Various wire screen type packings may be employed where the screens are woven rather than knitted. Other acceptable dispersers include perforated sheets and expanded metals, open flow cross channel structures which are co-woven with fiberglass or other materials such as polymers co-knit with the wire mesh expanded or perforated sheets. Additionally the multi-filament component may be catalytic. The multi-filament catalytic material may be polymers, such as sulfonated vinyl resin (e.g., Amberlyst) and catalytic metals such as Ni, Pt, Co, Mo, Ag.

The disperser comprises at least 50 volume % open space up to about 97 volume % open space. Dispersers are position within the reaction zone in the reactor. Thus, for example, the multi filament component and the structural element, e.g., knit wire, should comprise about 3 volume % to about 50 volume % of the total disperser, the remainder being open space.

Suitable dispersers include structured catalytic distillation packings which are intended to hold particulate catalysts, or structured distillation packings composed of a catalytically active material, such as that disclosed in U.S. Pat. No. 5,730,843 which is incorporated herein in its entirety and which discloses structures that have a rigid frame made of two substantially vertical duplicate grids spaced apart and held rigid by a plurality of substantially horizontal rigid members and a plurality of substantially horizontal wire mesh tubes mounted to the grids to form a plurality of fluid pathways among the tubes, said tubes being empty or containing catalytic or non catalytic materials; and structured packings which are catalytically inert which are typically constructed of corrugated metal bent at various angles, wire mesh which is crimped, or grids which are horizontally stacked one on top of the other, such as disclosed in U.S. Pat. No. 6,000,685 which is incorporated herein in its entirety and which discloses contact structures comprising a plurality of sheets of wire mesh formed into vee shaped corrugations having flats between the vees, said plurality of sheets being of substantially uniform size having the peaks oriented in the same direction and substantially in alignment, said sheets being separated by a plurality of rigid members oriented normally to and said resting upon said vees.

Other suitable dispersers include: (A) random or dumped distillation packings which are: catalytically inert dumped packings contain higher void fraction and maintain a relatively large surface area, such as, Berl Saddles (Ceramic), Raschig Rings (Ceramic), Raschig Rings (Steel), Pall rings (Metal), Pall rings (Plastic, e.g. polypropylene) and the like and catalytically active random packings which contain at least one catalytically active ingredient, such as Ag, Rh, Pd, Ni, Cr, Cu, Zn, Pt, Tu, Ru, Co, Ti, Au, Mo, V, and Fe as well as impregnated components such a metal-chelate complexes, acids such as phosphoric acid, or bonded, inorganic, powdered materials with catalytic activity; and (B) monoliths which are catalytically inert or active which are structures containing multiple, independent, vertical channels and may be constructed of various materials such as plastic, ceramic, or metals, in which the channels are typically square; however, other geometries could be utilized, being used as such are coated with catalytic materials.

The hydrocarbon feedstock undergoing alkylation by the method of the present invention is provided to the reaction zone in a continuous hydrocarbon phase containing effective amounts of olefinic and isoparaffinic starting materials which are sufficient for forming an alkylate product. The olefin:isoparaffin mole ratio in the total reactor feed should range from about 1:1.5 to about 1:30, and preferably from about 1:5 to about 1:15. Lower olefin:isoparaffin ratios may also be used.

The olefin component should preferably contain 2 to 16 carbon atoms and the isoparaffin component should preferably contain 4 to 12 carbon atoms. Representative examples of suitable isoparaffins include isobutane, isopentane, 3-methylhexane, 2-methylhexane, 2,3-dimethylbutane and 2,4-dimethylhexane. Representative examples of suitable olefins include butene-2, isobutylene, butene-1, propylene, pentenes, ethylene, hexene, octene, and heptene, merely to name a few and as described above may be oligomers of these olefins.

In the fluid process the system uses hydrofluoric or sulfuric acid catalysts under relatively low temperature conditions. For example, the sulfuric acid alkylation reaction is particularly sensitive to temperature with low temperatures being favored in order to minimize the side reaction of olefin polymerization. Petroleum refinery technology favors alkylation over polymerization because larger quantities of higher octane products can be produced per available light chain olefins. Acid strength in these liquid acid catalyzed alkylation processes is preferably maintained at 88 to 94% by weight using the continuous addition of fresh acid and the continuous withdrawal of spent acid. Other acids such as solid phosphoric acid may be used by supporting the catalysts within or on the packing material.

Preferably, the process of the present invention should incorporate relative amounts of acid and hydrocarbon fed to the top of the reactor in a volumetric ratio ranging from about 0.01:1 to about 2:1, and more preferably in a ratio ranging from about 0.05:1 to about 0.5:1. In the most preferred embodiment of the present invention, the ratio of acid to hydrocarbon should range from about 0.1:1 to about 0.3:1.

Additionally, the dispersion of the acid into the reaction zone should occur while maintaining the reactor vessel at a temperature ranging from about 0° F. to about 200° F., and more preferably from about 35° F to about 130° F. Similarly, the pressure of the reactor vessel should be maintained at a level ranging from about 0.5 ATM to about 50 ATM, and more preferably from about 0.5 ATM to about 20 ATM. Most preferably, the reactor temperature should be maintained within a range from about 40° F. to about 110° F. and the reactor pressure should be maintained within a range from about 0.5 ATM to about 5 ATM.

In general, the particular operating conditions used in the process of the present invention will depend to some degree upon the specific alkylation reaction being performed. Process conditions such as temperature, pressure and space velocity as well as the molar ratio of the reactants will affect the characteristics of the resulting alkylate product and may be adjusted in accordance with parameters known to those skilled in the art.

An advantage of operating at the boiling point of the present reaction system is that there is some evaporation which aids in dissipating the heat of reaction and making the temperature of the incoming materials closer to that of the materials leaving the reactor as in an isothermal reaction.

Once the alkylation reaction has gone to completion, the reaction mixture is transferred to a suitable separation vessel where the hydrocarbon phase containing the alkylate product and any unreacted reactants is separated from the acid. Since the typical density for the hydrocarbon phase ranges from about 0.6 g/cc to about 0.8 g/cc and since densities for the acid generally fall within the ranges of about 0.9 g/cc to about 2.0 g/cc, the two phases are readily separable by conventional gravity settlers. Suitable gravitational separators include decanters. Hydrocyclones, which separate by density difference, are also suitable.

One alkylation embodiment is shown in the FIGURE which is a simplified schematic representation of the apparatus and flow of the process. Such items as valves, reboilers, pumps, etc., have been omitted.

The reactor 10 is shown containing a disperser mesh 40. The present dispersers achieve radial dispersion of the fluid or fluidized materials in the reactor. The feed to the reactor comprises an olefin fed via line 12 such as n-butene and an isoparaffin (e.g., isobutane) fed via line 14 through line 52. Preferably a portion of the olefin is fed along the reactor via lines 16a, 16b, and 16c. A liquid acid catalyst such as $H_2SO_4$ is fed via line 56 and make-up acid may be supplied through line 38. The hydrocarbon reactants are fed to the reactor which is preferably a generally cylindrical column via line 58 and through appropriate dispersing means (not shown) into the disperser mesh 40, for example, a co-knit wire and fiberglass mesh.

The hydrocarbon reactants and non reactive hydrocarbons (e.g., normal butane) are intimately contacted with the acid catalyst as the alkylation proceeds. The reaction is exothermic. The pressure as well as the quantities of reactants are adjusted to keep the system components at the boiling point but partially in the liquid phase as the system components pass down flow through the reactor in mixed vapor/liquid phase and out through line 18 into decanter 30. In the decanter the system components are separated into an acid phase 46 containing the catalyst, a hydrocarbon phase 42 containing the alkylate, unreacted olefin and unreacted isoparaffin, and non reactive hydrocarbons and a vapor phase 44 which may contain some of each of the components and any lighter hydrocarbon components which are removed from the system via line 50 for further handling as appropriate.

Most of the acid phase is recycled via line 24 and 56 into the reactor. Make-up acid may be added via line 38 and build-up spent acid removed via line 48.

The hydrocarbon liquid phase is removed via line 22 with a portion recycled to the top of the reactor via line 28. The remainder of hydrocarbon phase is fed to distillation column 20 via line 26 where it is fractionated. Normal butane, if present in the feed, can be removed via line 36 and the alkylate product is removed via line 34. The overheads 32 are primarily unreacted isoalkane which is recycled via line 52 to the top of reactor 10.

Experimental Set up for Alkylation of Isoparaffin+Olefin

For the following examples the laboratory reactor is 15 feet high by 1.5 inches diameter. It is packed with varying amounts and types of packing material. The $H_2SO_4$ inventory is about 1 liter depending on the holdup of the packing used. The surge reservoir is about 3 liters and passes all the acid plus liquid hydrocarbon out the bottom to circulate a two-phase mixture with a single pump. Feeds are introduced at the top of the reactor to flow down with the recycle mixture. Vapor is produced by heat of reaction plus ambient heat gains and helps force the liquids down through the packing creating great turbulence and mixing. Most of the vapors are condensed after the reactor outlet. Uncondensed vapor and liquid hydrocarbon product passes through an acid de-entrainer then through the backpressure regulator to the de-isobutanizer. Mass flow meters are used for feed flows and a Doppler meter measures the circulation rate. Liquid products from the de-isobutanizer are weighed. However, the vent flow rate is estimated as being the difference between the mass flow metered feed in and the weighed liquid products out. GC analyzes all hydrocarbon products, including the vent. Titration is used for spent acid assay.

Operation

In the following examples the experimental unit circulates hydrocarbon and acid down flow at the boiling point of the hydrocarbons present. Pressure and temperature readings are logged electronically. The reactor outlet temperature and pressure are used to calculate the amount of $iC_4$ in the recycle hydrocarbon using an $iC_4$/Alkylate flash calculation.

A backpressure regulator that passes both product liquid and vapor to the de-isobutanizer tower, maintains the pressure. A small amount of $N_2$ may be used primarily to keep acid from backing up into the feed line. However, too much $N_2$ will cause a decrease in product quality by diluting reactive isoparaffin in the vapor phase.

The circulation pump in the experimental setup circulates both the acid emulsion layer and the liquid hydrocarbon layer. Alternatively, these two phases may be pumped separately.

The acid inventory is maintained by momentarily diverting the entire recycle through a measuring tube using a three-way valve. The trapped material settles in seconds to form two layers. The volume percent acid layer and hydrocarbon layer is then used in conjunction with the Doppler meter reading to estimate the volumetric circulation rates of both phases.

The DP (pressure higher at the top or reactor inlet) is maintained between 0 and 3 psi by manipulating the circulation rates and the heat balance around the unit. Different packing usually requires different vapor and liquid flow rates to load to the same DP. Most of the time, the ambient heat gains and the heat of reaction provide adequate vapor (mostly $iC_4$) loading.

Because of refrigeration constraints, about 1–3 lbs/hr of extra liquid $iC_4$ may be introduced with the feed to provide some trim cooling. This excess $iC_4$ is relatively small and does not significantly affect the $iC_4$/Olefin ratio since the circulating hydrocarbon rates are typically on the order of 100–200 pounds per hour. It is the circulating hydrocarbon flow rate and composition that dominates the $iC_4$ ratios to everything else.

Typical Operating Conditions for C4 Alkylation in the Examples

| Feed olefin | C4's |
|---|---|
| Olefin in - lbs/hr | 0.25–.50 |
| Alky out - lbs/hr | 0.50–1.2 |
| Rxn Temp out - F. | 50–60 |
| Rxn Psig out | 6–16 |
| DP - Psi | 0.5–3.0 |
| Recycle rates: | |
| Acid phase - L/min | 0.3–1 |
| HC phase - L/min | 1–3 |
| Wt % iC4 in HC recycle | 75–45 |
| Wt % H2SO4 in Spent acid | 83–89 |
| Wt % H2O in Spent acid | 2–4 |
| Fresh acid addition - lbs/gal alky | 0.3–0.5 |
| Packing Type | 1 or 2 - see notes below |
| Packing Hgt in feet | 10–15 |
| Pack density lbs/ft3 | 5–14 |

Notes:
1. Packing type 1 is .011 inch diameter 304 ss wire coknitted with 400 denier multifilament fiberglass thread every other stitch.
2. Packing type 2 is .011 inch diameter alloy 20 wire coknitted with 800 denier multifilament poly propylene yarn every other stitch.

EXAMPLE 1

| Refinery C4 Olefins used as feedstocks | | |
|---|---|---|
| To the Lab Unit: | Low iB | 38% iB in total olefins |
| methane | 0.02 | 0.00 |
| ethane | 0.00 | 0.00 |
| ethene | 0.00 | 0.00 |
| propane | 0.77 | 0.41 |
| propene | 0.14 | 0.16 |
| propyne | 0.02 | 0.00 |
| propadiene | 0.01 | 0.02 |
| iso-butane | 23.91 | 47.50 |
| iso-butene | 0.90 | 15.90 |
| 1-butene | 20.02 | 10.49 |
| 1,3-butadiene | 0.02 | 0.19 |
| n-butane | 22.63 | 10.79 |
| t-2-butene | 18.05 | 7.93 |
| 2,2-dm propane | 0.09 | 0.00 |
| 1-butyne | 0.00 | 0.01 |
| m-cyclopropane | 0.03 | 0.03 |
| c-2-butene | 12.09 | 5.43 |
| 1,2-butadiene | 0.00 | 0.01 |
| 3M-1-butene | 0.26 | 0.04 |
| iso-pentane | 0.98 | 0.02 |
| 1-pentene | 0.06 | 0.82 |
| 2M-1-butene | 0.01 | 0.01 |
| n-pentane | 0.01 | 0.03 |
| t-2-pentene | 0.00 | 0.08 |
| c-2-pentene | 0.00 | 0.00 |
| t-3-pentadiene | 0.00 | 0.08 |
| c-1,3-pentadiene | 0.00 | 0.00 |
| unknowns | 0.01 | 0.08 |
| | 100.00 | 100.00 |

Comparison of Refinery produced Alkylate with Lab Unit Results Using Similar Low iB C4 Feed

| | Plant A | Plant B | Lab 1 | Lab 2 |
|---|---|---|---|---|
| iC5 | 6.27 | 2.70 | 2.51 | 2.78 |
| 2,3-dmb | 4.05 | 2.84 | 2.80 | 3.02 |
| C6 | 1.63 | 1.19 | 1.00 | 1.15 |
| 2,2,3-tmb | 0.20 | 0.17 | 0.18 | 0.19 |
| C7 | 7.17 | 5.55 | 4.35 | 4.35 |
| TM C8 | 53.88 | 61.76 | 66.84 | 66.93 |
| DM C8 | 12.27 | 12.47 | 12.69 | 12.44 |
| TM C9 | 5.04 | 4.22 | 2.89 | 2.74 |
| DM C9 | 0.57 | 1.01 | 0.29 | 0.18 |
| TM C10 | 1.14 | 0.91 | 0.70 | 0.64 |
| UNK C10 | 0.51 | 0.54 | 0.29 | 0.29 |
| TM C11 | 0.99 | 0.77 | 0.69 | 0.71 |
| UNK C11 | 1.09 | 0.02 | 0.00 | 0.00 |
| C12 | 4.37 | 1.71 | 4.72 | 4.60 |
| C13 | 0.00 | 1.58 | 0.00 | 0.00 |
| C14 | 0.03 | 1.57 | 0.05 | 0.00 |
| C15 | 0.00 | 0.13 | 0.00 | 0.00 |
| HV'S | 0.05 | 0.04 | 0.00 | 0.00 |
| UNK | 0.74 | 0.83 | 0.00 | 0.00 |
| sum | 100.00 | 100.00 | 100.00 | 100.00 |
| Av MW | 110.2 | 113.4 | 112.8 | 112.4 |
| Bromine no. | <1 | <1 | <1 | <1 |
| Total Sulfur ppm | <10 | <10 | <10 | <10 |
| TOTAL % TM | 61.05 | 67.66 | 71.12 | 71.01 |
| TM C8/DM C8 (ratio) | 4.39 | 4.95 | 5.27 | 5.38 |
| TM C9/DM C9 (ratio) | 8.85 | 4.19 | 10.08 | 15.57 |

Typical Vent Analysis:

| | wt % |
|---|---|
| hydrogen | 0.000 |
| oxygen | 0.124 |
| nitrogen | 3.877 |
| methane | 0.019 |
| carbon monoxide | 0.000 |
| carbon dioxide | 0.000 |
| ethane | 0.000 |
| ethene | 0.000 |
| ethyne | 0.000 |
| propane | 1.066 |
| propene | 0.000 |
| propadiene | 0.000 |
| iso-butane | 81.233 |
| iso-butene | 0.021 |
| 1-butene | 0.000 |
| 1,3-butadiene | 0.031 |
| n-butane | 3.398 |
| t-2-butene | 0.000 |
| m-cyclopropane | 0.000 |
| c-2-butene | 0.000 |

-continued

| | wt % |
|---|---|
| iso-pentane | 0.968 |
| 1-pentene | 0.000 |
| n-pentane | 0.000 |
| C5+ | 0.391 |

EXAMPLE 2

Effect of Isobutylene (iB) on Alky Quality

| | 100% iB | 38% iB | lab 1 low iB |
|---|---|---|---|
| iC5 | 3.66 | 3.97 | 2.78 |
| 2,3-dmb | 3.60 | 3.56 | 3.02 |
| C6 | 1.42 | 0.52 | 1.15 |
| 2,2,3-tmb | 0.40 | 0.23 | 0.19 |
| C7 | 5.27 | 5.08 | 4.35 |
| TM C8 | 50.79 | 56.95 | 66.93 |
| DM C8 | 11.77 | 12.64 | 12.44 |
| TM C9 | 6.07 | 4.22 | 2.74 |
| DM C9 | 0.58 | 0.45 | 0.18 |
| TM C10 | 2.06 | 1.33 | 0.64 |
| UNK C10 | 1.14 | 0.67 | 0.29 |
| TM C11 | 2.54 | 1.28 | 0.71 |
| UNK C11 | 1.00 | 0.00 | 0.00 |
| C12 | 8.30 | 8.99 | 4.60 |
| C13 | 0.07 | 0.00 | 0.00 |
| C14 | 0.28 | 0.14 | 0.00 |
| C15 | 0.12 | 0.00 | 0.00 |
| HV'S | 0.38 | 0.00 | 0.00 |
| UNK | 0.54 | 0.00 | 0.00 |
| sum | 100.00 | 100.00 | 100.00 |
| Av MW | 115.1 | 113.8 | 112.4 |
| Bromine no. | ~1 | <1 | <1 |
| Total Sulfur ppm | <10 | <10 | <10 |
| TOTAL % TM | 61.46 | 63.77 | 71.12 |
| TM C8/DM C8 | 4.31 | 4.51 | 5.27 |
| TM C9/DM C9 | 10.51 | 9.34 | 10.08 |

EXAMPLE 3

Propylene + iC4 Alkylation

| Sample Point | product |
|---|---|
| propane | 0.01 |
| iso-butane | 9.25 |
| n-butane | 0.32 |
| iso-pentane | 0.97 |
| n-pentane | 0.00 |
| 2,3-dm butane | 2.07 |
| 2M-pentane | 0.30 |
| 3M-pentane | 0.14 |
| n-hexane | 0.00 |
| 2,4-dm pentane | 15.59 |
| 2,2,3-tm butane | 0.04 |
| 3,3-dm pentane | 0.01 |
| cyclohexane | 0.00 |
| 2M-hexane | 0.34 |
| 2,3-dm pentane | 48.97 |
| 1,1-dm cyclopentane | 0.00 |
| 3M-hexane | 0.35 |
| 2,2,4-tm pentane | 3.42 |

-continued

Propylene + iC4 Alkylation

| Sample Point | product |
|---|---|
| n-heptane | 0.00 |
| 2,5-dm hexane | 0.37 |
| 2,4-dm hexane | 0.56 |
| 2,3,4-tm pentane | 1.52 |
| 2,3,3-tm pentane | 1.21 |
| 2,3-dm hexane | 0.64 |
| 2,2,5-tm hexane | 0.68 |
| 2,3,4-tm hexane | 0.13 |
| 2,2-dm heptane | 0.01 |
| 2,4-dm heptane | 0.03 |
| 2,6-dm heptane | 0.03 |
| 2,2,4-tm-heptane | 1.83 |
| 3,3,5-tm-heptane | 1.70 |
| 2,3,6-tm-heptane | 1.16 |
| 2,3,5-tm-heptane | 0.16 |
| tm-heptane | 1.00 |
| 2,2,6-trimethyloctane | 2.32 |
| C8s | 0.20 |
| C9s | 0.20 |
| C10s | 0.98 |
| C11s | 1.62 |
| C12s | 1.73 |
| C13s | 0.09 |
| C14s | 0.05 |
| C15s | 0.01 |
| unknowns | 0.01 |
| heavies | 0.00 |
| | 100.00 |

EXAMPLE 4

Isobutane + pentene 1 alkylation product

| | Wt % |
|---|---|
| C5 | 5.03 |
| 2,3-dmb | 0.74 |
| C6 | 0.35 |
| DM C7 | 1.14 |
| C7 | 0.17 |
| TM C8 | 22.26 |
| DM C8 | 3.70 |
| TM C9 | 52.40 |
| DM C9 | 6.72 |
| TM C10 | 1.51 |
| UNK C10 | 0.56 |
| TM C11 | 0.16 |
| UNK C11 | 0.38 |
| C12 | 3.68 |
| C13 | 0.33 |
| C14 | 0.11 |
| C15 | 0.08 |
| HV'S | 0.03 |
| UNK | 0.63 |
| | 100.00 |
| Avg MW | 120.0 |
| expected MW | 128 |
| feed olefin #/hr | 0.25 |
| Alky product #/hr | 0.47 |

EXAMPLE 5

Oligomerization product from C4 feedstock with 38% iB in total olefins. (This product was in turn used as the olefin feed to the lab Alkylation unit)

|  |  |
|---|---|
| iso-butane | 48.8 |
| iso-butene + 1-butene | 1.6 |
| n-butane | 11.2 |
| t-2-butene | 14.3 |
| c-2-butene | 6.5 |
| iso-pentane | 1.0 |
| t-2-pentene | 0.1 |
| unknowns | 1.5 |
| 2,4,4-tm-1-pentene | 4.7 |
| 2,4,4-tm-2-pentene | 1.3 |
| other C8's | 3.4 |
| grouped C12's | 4.4 |
| grouped C16's | 1.2 |
|  | 100.0 |

Oligomerization effect on Alky products using C4 feed with iB=38% of Olefins

|  | before | after |
|---|---|---|
| iC5 | 3.97 | 2.39 |
| 2,3-dmb | 3.56 | 2.87 |
| C6 | 0.52 | 1.17 |
| 2,2,3-tmb | 0.23 | 0.20 |
| C7 | 5.08 | 4.95 |
| TM C8 | 56.95 | 58.34 |
| DM C8 | 12.64 | 12.80 |
| TM C9 | 4.22 | 4.15 |
| DM C9 | 0.45 | 0.35 |
| TM C10 | 1.33 | 1.29 |
| UNK C10 | 0.67 | 0.57 |
| TM C11 | 1.28 | 1.41 |
| UNK C11 | 0.00 | 0.00 |
| C12 | 8.99 | 9.41 |
| C13 | 0.00 | 0.00 |
| C14 | 0.14 | 0.11 |
| C15 | 0.00 | 0.00 |
| HV'S | 0.00 | 0.00 |
| UNK | 0.00 | 0.00 |
| sum | 100.00 | 100.00 |
| Av MW | 113.8 | 115.1 |
| Bromine no. | <1 | <1 |
| Total Sulfur ppm | <10 | <10 |
| TOTAL % TM | 63.77 | 65.19 |
| TM C8/DM C8 | 4.51 | 4.56 |
| TM C9/DM C9 | 9.34 | 11.75 |
| Operating conditions: |  |  |
| Olefin in - lbs/hr | .25 | .25 |
| Alky out - lbs/hr | .53 | .53 |
| Rxn Temp out - F. | 52.0 | 52.2 |
| Rxn Psig out | 12.2 | 11.8 |
| DP - Psi | ~1 | ~1 |
| Recycle rates: |  |  |
| Acid phase - L/min | 1.0 | 1.0 |
| HC phase - L/min | 2.6 | 2.6 |
| % | 69 | 67 |
| iC4 in HC recycle |  |  |
| Packing Type | 2 | 2 |
| Packing Hgt in feet | 15 | 15 |
| Pack density lbs/ft3 | 7 | 7 |

EXAMPLE 6

Alkylate quality from Isobutene + Isobutane or Oligomers of iB + iC4.

|  | iB | DIB | TIB+ |
|---|---|---|---|
| IC5 | 3.66 | 3.97 | 3.41 |
| 2,3-dmb | 3.60 | 3.70 | 3.18 |
| C6 | 1.42 | 1.36 | 1.53 |
| 2,2,3-tmb | 0.40 | 0.38 | 0.27 |
| C7 | 5.27 | 4.96 | 6.39 |
| TM C8 | 50.79 | 47.93 | 38.35 |
| DM C8 | 11.77 | 8.92 | 12.91 |
| TM C9 | 6.07 | 6.60 | 10.31 |
| DM C9 | 0.58 | 0.81 | 1.10 |
| TM C10 | 2.06 | 3.09 | 3.29 |
| UNK C10 | 1.14 | 1.18 | 1.35 |
| TM C11 | 2.54 | 2.53 | 2.72 |
| UNK C11 | 1.00 | 1.79 | 0.00 |
| C12 | 8.30 | 10.51 | 14.97 |
| C13 | 0.07 | 0.31 | 0.07 |
| C14 | 0.28 | 1.47 | 0.14 |
| C15 | 0.12 | 0.29 | 0.00 |
| HV'S | 0.38 | 0.19 | 0.00 |
| UNK | 0.54 | 0.01 | 0.00 |
| Sum | 100.00 | 100.00 | 100.00 |
| Av MW | 115.1 | 117.0 | 118.1 |
| Bromine no. | ~1 | ~1 | ~1 |
| Total Sulfur ppm | <10 | <10 | <10 |
| TOTAL % TM | 61.46 | 60.15 | 54.67 |
| TM C8/DM C8 | 4.31 | 5.37 | 2.97 |
| TM C9/DM C9 | 10.51 | 8.15 | 9.37 |
| Operating conditions: |  |  |  |
| Feed olefin | iB | DIB | TIB+ |
| Olefin in - lbs/hr | 0.25 | 0.40 | 0.25 |
| Alky out - lbs/hr | 0.49 | 0.78 | 0.48 |
| Rxn Temp out - F. | 52 | 51.6 | 51.7 |
| Rxn psig out | 13 | 13.5 | 5.7 |
| DP - psi | 2.5 | 1.1 | ~1 |
| Recycle rates: |  |  |  |
| Acid phase- L/min | 0.8 | 0.5 | 1.0 |
| HC phase - L/min | 1.8 | 1.4 | 3.0 |
| % | 73 | 76 | 45 |
| iC4 in HC recycle |  |  |  |
| Packing Type | 1 | 1 | 2 |
| Packing Hgt in feet | 10 | 10 | 15 |
| Pack density lbs/ft3 | 6 | 6 | 7 |

EXAMPLE 7

Expected vs. actual alkylation product MW's and moles iC4 uptake with various olefins (e.g. in theory 1 mole of C6 olefin should react with 1 mole of iC4 to form a C10 alkylate; MW=142)

Results indicate depolymerization generating more and lower MW olefins that combine with additional iC4.

|  | Moles iC4 uptake per mole Olefin fed | | Average product MW | |
|---|---|---|---|---|
| Olefin | Expected | Actual | Expected | Actual |
| Hexene-1 | 1.0 | 1.2 | 142 | 129 |
| Octene-1 | 1.0 | 1.4 | 170 | 135 |
| Di-isobutylene | 1.0 | 1.8 | 170 | 122 |
| Tri-isobutylene+ | 1.0 | 2.6 | 226 | 123 |

EXAMPLE 8

| Isobutane + pentene 1 alkylation product | Wt % |
|---|---|
| IC5 | 5.03 |
| 2,3-dmb | 0.74 |
| C6 | 0.35 |
| DM C7 | 1.14 |
| C7 | 0.17 |
| TM C8 | 22.26 |
| DM C8 | 3.70 |
| TM C9 | 52.40 |
| DM C9 | 6.72 |
| TM C10 | 1.51 |
| UNK C10 | 0.56 |
| TM C11 | 0.16 |
| UNK C11 | 0.38 |
| C12 | 3.68 |
| C13 | 0.33 |
| C14 | 0.11 |
| C15 | 0.08 |
| HV'S | 0.03 |
| UNK | 0.63 |
| | 100.00 |
| Avg MW | 123.2 |
| expected MW | 128 |
| feed olefin #/hr | 0.25 |
| Alky product #/hr | 0.47 |

The invention claimed is:

1. A paraffin alkylation process comprising contacting an oligomer comprising at least two constituent olefins with an isoalkane in the presence of hydrofluoric or sulfuric acid as the alkylation catalyst under alkylation conditions wherein said oligomer is disassociated into its constituent olefins which react with said isoalkene and recovering a product comprising an alkylate corresponding to the alkylation product of said isoalkane and said constituent olefins.

2. The process according to claim 1 wherein said oligomer comprises tertiary olefin constituents.

3. The process according to claim 2 wherein said oligomer comprises 6 to 16 carbon atoms.

4. The process according to claim 3 wherein said isoalkane comprises 4 to 5 carbon atoms.

5. The process according to claim 4 wherein said oligomer comprises an isobutene constituent.

6. The process according to claim 1 wherein said olefin comprises an oligomer having 6 carbon atoms.

7. The process according to claim 4 wherein said oligomer comprises an isoamylene constituent.

8. The process according to claim 4 wherein said tertiary olefin comprises isobutene and isoamylene constituents.

9. The process according to claim 5 wherein said isoalkane comprises isobutane.

10. The process according to claim 5 wherein said catalyst is sulfuric acid.

11. The process according to claim 5 wherein said catalyst is hydrofluoric acid.

* * * * *

UNITED STATES PATENT AND TRADEMARK OFFICE
CERTIFICATE OF CORRECTION

| | | |
|---|---|---|
| PATENT NO. | : 6,995,296 B2 | Page 1 of 1 |
| APPLICATION NO. | : 10/870104 | |
| DATED | : February 7, 2006 | |
| INVENTOR(S) | : Lawrence A. Smith, Jr. et al. | |

It is certified that error appears in the above-identified patent and that said Letters Patent is hereby corrected as shown below:

Column 16:

In claim 1, line 7, change "isoalkene" to read "--- isoalkane ---."

Signed and Sealed this

Fifteenth Day of August, 2006

JON W. DUDAS
*Director of the United States Patent and Trademark Office*